United States Patent
Comment et al.

(10) Patent No.: US 8,034,027 B2
(45) Date of Patent: Oct. 11, 2011

(54) INFUSION PUMP WITH PHASE SEPARATOR

(75) Inventors: Arnaud Comment, Lausanne (CH); Jacques Van Der Klink, Echichens (CH)

(73) Assignee: Ecole Polytechnique Federale De Lausanne (EPPL), Lausanne (CH)

( * ) Notice: Subject to any disclaimer, the term of this patent is extended or adjusted under 35 U.S.C. 154(b) by 85 days.

(21) Appl. No.: 12/119,037

(22) Filed: May 12, 2008

(65) Prior Publication Data
US 2008/0287875 A1    Nov. 20, 2008

Related U.S. Application Data

(60) Provisional application No. 60/938,193, filed on May 16, 2007.

(51) Int. Cl.
*A61M 37/00* (2006.01)
*A61M 1/00* (2006.01)

(52) U.S. Cl. ............ 604/131; 604/122; 604/141

(58) Field of Classification Search .......... 604/131, 604/65–67, 140, 141, 143, 147, 151–154, 604/69–70

See application file for complete search history.

(56) References Cited

U.S. PATENT DOCUMENTS

| | | | | |
|---|---|---|---|---|
| 3,727,614 A | * | 4/1973 | Kniazuk | 604/115 |
| 5,591,251 A | * | 1/1997 | Brugger | 95/242 |
| 6,650,929 B1 | * | 11/2003 | Nemoto et al. | 600/431 |
| 2002/0107501 A1 | * | 8/2002 | Smith et al. | 604/500 |
| 2004/0019313 A1 | * | 1/2004 | Childers et al. | 604/5.01 |
| 2005/0101934 A1 | * | 5/2005 | Meiser et al. | 604/508 |

* cited by examiner

*Primary Examiner* — Nicholas D Lucchesi
*Assistant Examiner* — Rebecca E Eisenberg
(74) *Attorney, Agent, or Firm* — Nixon & Vanderhye P.C.

(57) ABSTRACT

An infusion pump comprising a substance and pushing fluid inlet, a substance outlet, a central chamber communicating with said inlet and said outlet, and injecting means for injecting a substance into a biological object, wherein the infusion pump further includes a pushing fluid outlet in communication with the central chamber in such a way as to allow a pushing fluid to exhaust the pump. The outlet of the infusion pump is advantageously connected to the proximal end of a catheter, the distal end being inserted into the biological object. A sensor, e.g., an optical device, is preferably placed at the outlet of the infusion pump and checks that the outlet is free of gas. The infusion pump is preferably remotely controlled so that it can be placed in limited access locations. It is also preferably computer controlled.

16 Claims, 2 Drawing Sheets

INFUSION PUMP WITH PHASE SEPARATOR

CROSS REFERENCE TO RELATED APPLICATION

This application claims the benefit of U.S. Provisional Application No. 60/938,193 filed on 16 May 2007, incorporated herein by reference in its entirety.

FIELD OF THE INVENTION

The present invention relates to injection devices for injecting a substance into a biological object such as a tissue, an organ, an animal or a human being, wherein the substance to be injected is pushed by a pushing fluid such as gas.

BACKGROUND OF THE INVENTION

When using imaging, tomography or spectroscopy techniques such as magnetic resonance (MR), it is very useful and sometimes necessary to inject a liquid or a colloidal suspension into a tissue, an organ, an animal or a human before, during or after an experiment or an examination. The delay between the preparation and the infusion of the liquid or the colloidal suspension into a tissue, an organ, an animal or a human located inside the imaging, tomography or spectroscopy apparatus is a critical issue when the liquid or the colloidal suspension has short-lasting physical or chemical properties.

A first approach to infuse a liquid or a colloidal suspension with short-lasting physical or chemical properties is to collect the liquid or the colloidal suspension in a syringe and to quickly administrate it into the biological object. This is the way proposed for instance by J. H. Ardenkjaer-Larsen et al. to infuse hyperpolarized liquids for MR investigations (see WO 02/37132). WO 99/35508 very superficially discusses an idea of applying pressure to carry hyperpolarized material from a container to a patient undergoing MR examination. Practically such a procedure is difficult to implement because it requires at least three conditions, namely: a) a high-speed transfer of the material from the preparation apparatus to the imaging, tomography or spectroscopy apparatus (due to the short-lasting physical or chemical properties of the material), b) a relatively slow infusion speed (in order to avoid damage in the biological object), and c) an absence of gas in the infusion line (which could harm the biological object under examination). It should also be noted that if the biological object is placed in a location with limited access such as in a narrow bore MR magnet, a direct infusion with a syringe is hardly possible. WO 99/35508 does not discuss and consequently does not offer a solution to this complex procedure.

An objective of the present invention is to meet the above cited three conditions.

SUMMARY OF THE INVENTION

This objective is achieved with an infusion pump comprising a substance and pushing fluid inlet, a substance outlet, a central chamber communicating with said inlet and said outlet, and injecting mean-s for injecting a substance into a biological object, wherein the infusion pump further includes a pushing fluid outlet in communication with the central chamber in such a way as to allow a pushing fluid to exhaust the pump.

The outlet of the infusion pump is advantageously connected to the proximal end of a catheter, the distal end being inserted into the biological object. A sensor, e.g., an optical device, is preferably placed at the outlet of the infusion pump and checks that the outlet is free of gas. The infusion pump is preferably remotely controlled so that it can be placed in limited access locations. It is also preferably computer controlled.

DESCRIPTION OF THE PREFERRED EMBODIMENT

Figure 1:
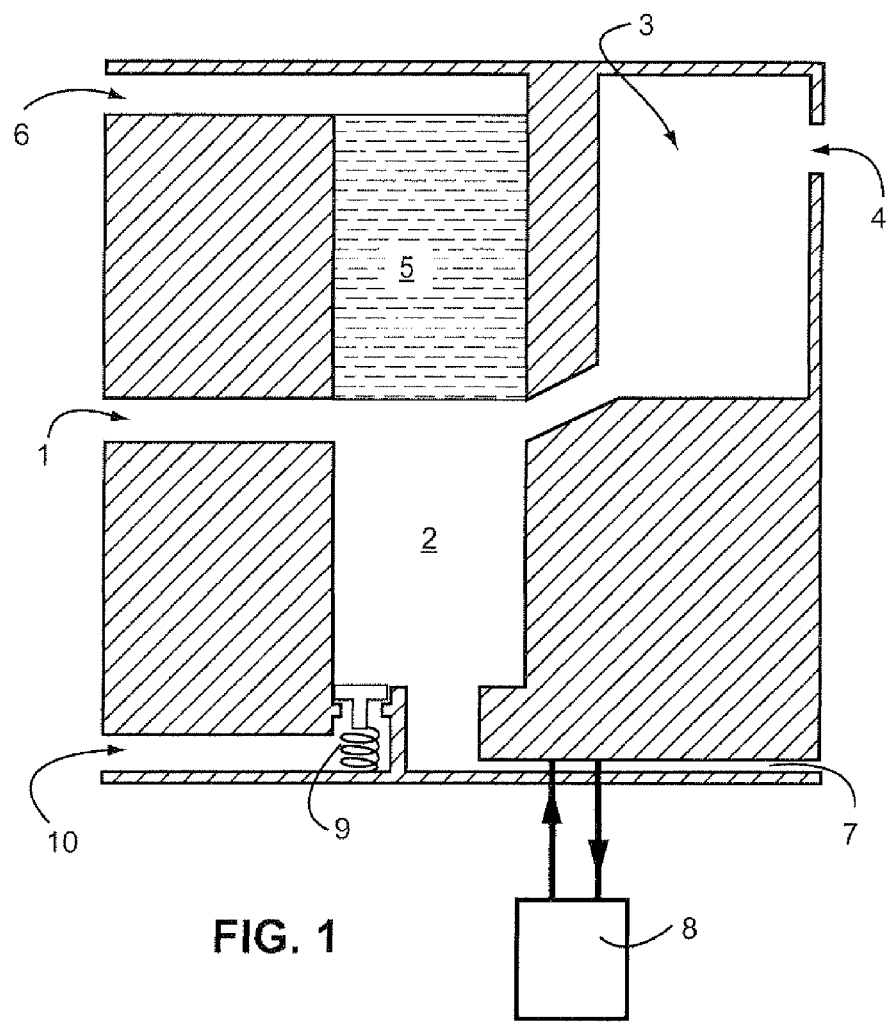
FIG. 1 shows a schematic cross-sectional view of an embodiment of the phase separator/infusion pump according to the invention.

FIG. 1 shows a phase separator/infusion pump with three inlet ports 1,6,10, one outlet port 7, and one or more overflow chambers 3. The material (liquid or solid) is pushed into the pump through the central inlet port 1 by pressurized gas. The central inlet port 1 is preferably connected to an inelastic tube that can withstand a gas pressure of several bars. The material is collected in the central chamber 2 while the gas used to push the material into the pump escapes through the exhaust port 4 preferably located on the side or above the overflow chambers 3. The overflow chamber 3 is designed so that the fraction of the material that could be propelled outside of the central chamber 2 by the pressurized gas will flow back into the central chamber 2 once the pressurized gas flow is stopped. Therefore, the channel connecting the overflow chamber 3 to the central chamber 2 should preferably be inclined with the largest possible inclination. The channel should preferably not face the inlet port 1 as illustrated in FIG. 1, but rather be placed in a vertical plane perpendicular to the inlet port main axis, such as to avoid a large amount of material to be pushed into the overflow chamber 3 by the pressurized gas coming from the inlet port 1. If the material introduced in the central chamber 2 is in solid form, a calculated amount of solvent can be introduced via the exhaust port 4 in order to dissolve or melt the material.

Once the required quantity of material has been introduced inside the central chamber 2 and the pressurized gas flow has been stopped, the displacement piston 15 (see FIG. 2) is moved downwards by injecting a fluid 5 through the displacement port 6. Subsequently, the central chamber 2 becomes isolated from the central inlet port 1 and the overflow chamber 3 and the material is infused through the infusion port 7. Rubber seals might be added on the piston 15 to insure proper sealing. A small extra volume is preferably added between the central chamber 2 and the infusion port 7 such as to forbid potential gas bubbles that could be formed on the bottom surface of the piston 15 to reach the infusion port 7. An optical sensor 8 checks for the potential presence of gas at the infusion port 7 and preferably stops the infusion if a gas bubble of non-negligible size is detected. The optical sensor 8 is preferably composed of a solid state light source such as a light emitting diode illuminating the infusion port through an optical fiber and a light sensor collecting the diffused light and measuring its intensity.

Optionally, to allow for multiple infusions without having to disconnect the outlet line from the infusion port 7, a valve 9 connected to a preferably elastic fixation (e.g. spring or rubber band) can be added at the bottom of the central chamber 2. This valve 9 is forced close before and during the infusion but opens once the piston 15 is lifted. When the valve 9 is open, gas, preferably at atmospheric pressure, enters the central chamber 2 from the gas entry port 10 and prevents the creation of vacuum in the central compartment, which would lead to suction on the infusion port.

The entire procedure is preferably remotely controlled since it might be desirable to place the device in locations with limited access. The entire procedure is also preferably fully automated through computer control. In particular, the introduction of material, and therefore the control of the pressurized gas, should be preferably carefully synchronized with the injection of the fluid at the displacement port 6. Moreover, the infusion should preferably be automatically stopped as soon as the optical sensor 8 has detected air at the infusion port.

The invention is illustrated with reference to the following non-limiting Examples.

Example 1

The device can be used to infuse hyperpolarized material into tissues, organs, animals or humans under MR investigation. A catheter or a similar infusion device is inserted into the biological object placed inside the MR magnet. The catheter is connected to the infusion port 7 of an embodiment of the phase separator/infusion pump described above.

Figure 2:
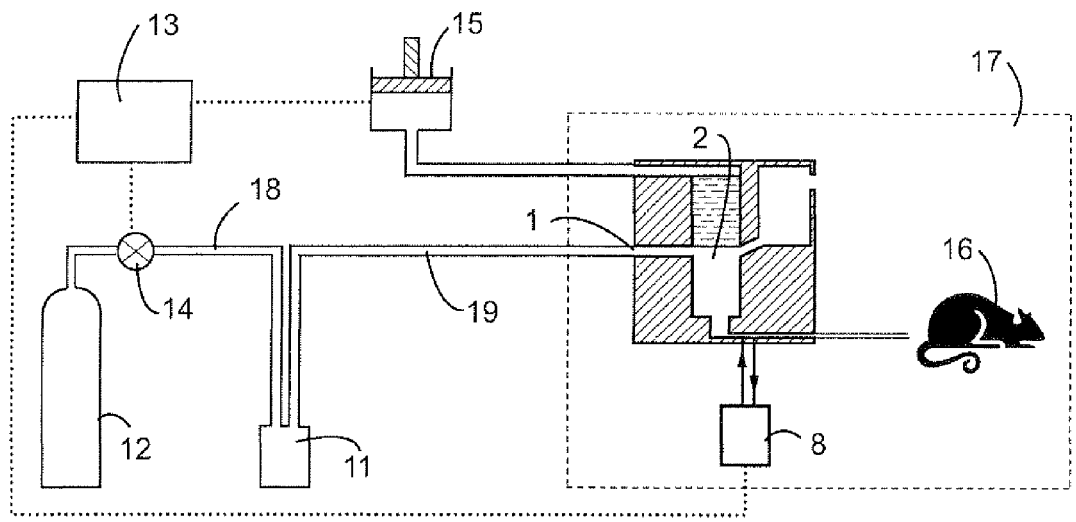
FIG. 2 shows schematically a complete assembly for an in vivo MR investigation which includes the pump of FIG. 1.

An embodiment of a complete assembly is illustrated in FIG. 2. A pressurized gas container 12 is connected to a sample container 11 through a tube 18. A valve 14 controls the introduction of the gas flow in the circuit. The material to be infused is prepared in the sample container 11. Once the valve 14 is opened, the gas flow pushes the material into the phase separator/infusion pump 1,2 in which the material is collected and separated from the gas. Once the valve 14 is closed, the material is infused into the biological object 16 under examination by applying a pressure on the displacement piston 5 of the infusion pump using the remote pumping system. An optical sensor 8 checks for the potential presence of gas at the infusion port 7 and automatically stops the infusion if a gas bubble of non-negligible size is detected.

In most cases it is advantageous to place the device as close as possible to the biological object. This imposes some constraints on the materials with which the device is realized. For this particular use, the preferred embodiment of the device is made of plastic materials since it can then be placed in a high-magnetic field environment such as inside the bore of an MR magnet 17. The device is remotely controlled since it is placed next to the subject under examination in a narrow bore MR magnet and it is essentially impossible to directly access it. The procedure is also preferably computer 13 controlled.

Figure 3:
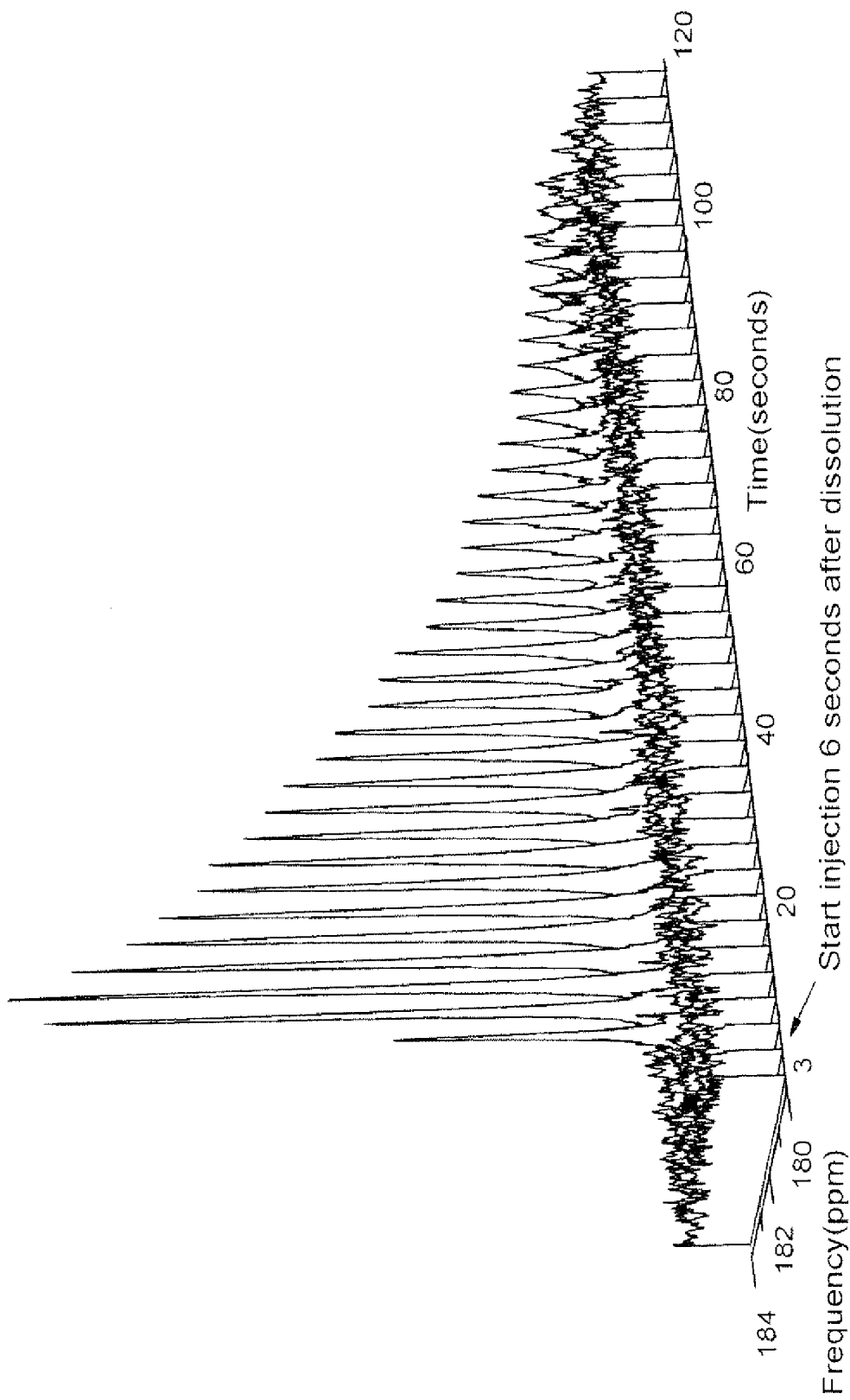
FIG. 3 shows the time evolution of an in vivo rat brain $^{13}$C signal measured by MR after injection of a 0.3M hyperpolarized $^{13}$C-labeled acetate solution with an embodiment of a phase separator/infusion pump.

The results of an experiment performed in a 9.4T MR imager on a rat after the infusion of a hyperpolarized $^{13}$C-labeled acetate solution using an embodiment of the full setup described above is shown in FIG. 3.

Example 2

The device can be used for the infusion of MR contrast agents into a tissue, organ, animal or human installed inside an MR magnet bore. The procedure and the setup are essentially identical to the procedure and the setup described in Example 1.

Example 3

The device can be used for the infusion of MR contrast agents following the infusion of hyperpolarized material into a tissue, organ, animal or human installed inside an MR magnet bore. The procedure and the setup are essentially identical to the procedure and the setup described in Example 1.

The invention claimed is:

1. An infusion pump comprising:
an inlet for a substance and a pushing fluid,
an outlet adapted for allowing the substance to flow through,
a central chamber communicating with said inlet and said outlet, and
an injecting means for injecting the substance into a biological object,
wherein said infusion pump further includes a pushing fluid outlet in communication with said central chamber in such a way as to allow the pushing fluid to exhaust said pump, and
wherein said injecting means include an injecting fluid, an injecting fluid inlet, and a piston, and said injecting means furthermore being in fluid communication with said central chamber.

2. An infusion pump according to claim 1 further comprising a vacuum prevention means which comprise an atmospheric port and a one-way valve located between said central chamber and said atmospheric port, said one-way valve being arranged in a way as to exclusively allow atmospheric air to enter said central chamber.

3. An infusion pump according to claim 1 further comprising an overflow chamber in communication with said central chamber.

4. An infusion pump according to claim 3 wherein both chambers communicate through a channel which forms a slope.

5. An infusion pump according to claim 4 wherein said channel is perpendicular with respect to said inlet for a substance and a pushing fluid.

6. An infusion pump according to claim 1 further comprising a pushing fluid and/or injecting fluid sensor which is located between said central chamber and said substance outlet.

7. An infusion pump according to claim 6 wherein said sensor is a gas sensor.

8. An assembly for injecting a substance into a biological object comprising successively a pushing fluid container, a pushing fluid line, a substance container, a substance and pushing fluid line and an infusion pump as defined in claim 1, each of said elements communicating with its adjacent element.

9. An infusion pump assembly comprising:
a substance,
a pushing fluid,
an inlet for the substance and the pushing fluid,
an outlet adapted for allowing the substance to flow through,
a central chamber communicating with said inlet and said outlet,
an injecting means for injecting the substance into a biological object,
wherein said infusion pump further includes a pushing fluid outlet in communication with said central chamber in such a way as to allow the pushing fluid to exhaust said pump, and
wherein said injecting means include an injecting fluid, an injecting fluid inlet, and a piston, said injecting means furthermore being in fluid communication with said central chamber.

10. An infusion pump assembly according to claim 9 further comprising a vacuum prevention means comprising an atmospheric port and a one-way valve located between said central chamber and said atmospheric port, said one-way valve being arranged in a way as to exclusively allow atmospheric air to enter said central chamber.

11. An infusion pump assembly according to claim 9 further comprising an overflow chamber in communication with said central chamber.

12. An infusion pump assembly according to claim 11 wherein both chambers communicate through a channel which forms a slope.

13. An infusion pump assembly according to claim 11 wherein said channel is perpendicular with respect to said inlet for the substance and the pushing fluid.

14. An infusion pump assembly according to claim 9 further comprising a pushing fluid and/or injecting fluid sensor which is located between said central chamber and said substance outlet.

15. An infusion pump assembly according to claim 14 wherein said sensor is a gas sensor.

16. An assembly for injecting a substance into a biological object comprising successively a pushing fluid container element, an adjacent pushing fluid line element, an adjacent substance container element, a adjacent substance and pushing fluid line element, and an adjacent infusion pump assembly as defined in claim 9, each of said elements and pump assembly communicating with its adjacent element and pump assembly.

* * * * *

UNITED STATES PATENT AND TRADEMARK OFFICE
CERTIFICATE OF CORRECTION

| | |
|---|---|
| PATENT NO. | : 8,034,027 B2 |
| APPLICATION NO. | : 12/119037 |
| DATED | : October 11, 2011 |
| INVENTOR(S) | : Comment et al. |

Page 1 of 1

It is certified that error appears in the above-identified patent and that said Letters Patent is hereby corrected as shown below:

On the Title Page

Item 73, change "Ecole Polytechnique Federale De Lausanne (EPPL)" to --Ecole Polytechnique Federale De Lausanne (EPFL)--

Signed and Sealed this
Tenth Day of March, 2015

Michelle K. Lee
*Deputy Director of the United States Patent and Trademark Office*